United States Patent [19]

Arai et al.

[11] Patent Number: 4,892,731

[45] Date of Patent: Jan. 9, 1990

[54] BIOLOGICAL INTESTINAL ANTISEPTICS

[75] Inventors: Tadashi Arai, 50-6 Nogata, 6-Chome, Nakano-ku, Tokyo; Mamoru Tanaka, Nagano; Akio Maeda, Chiba, all of Japan

[73] Assignee: Tadashi Arai, Tokyo, Japan

[21] Appl. No.: 243,038

[22] PCT Filed: Dec. 11, 1987

[86] PCT No.: PCT/JP87/00970

§ 371 Date: Aug. 9, 1988

§ 102(e) Date: Aug. 9, 1988

[30] Foreign Application Priority Data

Dec. 11, 1986 [JP] Japan .................................. 61-293349

[51] Int. Cl.$^4$ ............................................. A61K 39/08
[52] U.S. Cl. .................................. 424/93; 435/252.7; 435/842
[58] Field of Search ........................ 424/93; 435/252.7

[56] References Cited

PUBLICATIONS

Maeda et al., Journal of General Microbiology (1986), 132, 2271-2275.

Primary Examiner—Howard E. Schain
Assistant Examiner—Choon P. Koh
Attorney, Agent, or Firm—Lalos & Keegan

[57] ABSTRACT

Cells or endospores of a butyric-acid bacterium *Clostridium butyricum* MII588-Sens 1 strain, or cells or endospores of a butyric-acid bacterium *Clostridium butyricum* MII588-Res 1 strain are effective as a biological intestinal antiseptic.

1 Claim, 6 Drawing Sheets

●; VIABLE CELL COUNT OF VIBRIO PARAHAEMOLYTICUS IN THE SINGLE CULTURE

○; VIABLE CELL COUNT OF VIBRIO PARAHAEMOLYTICUS IN THE MIXED CULTURE

▲; VIABLE CELL COUNT OF CLOSTRIDIUM BUTYRICUM MII588-RES 1 IN THE MIXED CULTURE

●; VIABLE CELL COUNT OF SALMONELLA ENTERITIDIS IN THE SINGLE CULTURE
○; VIABLE CELL COUNT OF SALMONELLA ENTERITIDIS IN THE MIXED CULTURE
▲; VIAL CELL COUNT OF CLOSTRIDIUM BUTYRICUM MIII588-SENS 1 IN THE MIXED CULTURE

●; VIABLE CELL COUNT OF ESCHERICHIA COLI IN THE SINGLE CULTURE

○; VIABLE CELL COUNT OF ESCHERICHIA COLI IN THE MIXED CULTURE

▲; VIABLE CELL COUNT OF CLOSTRIDIUM BUTYRICUM MII588-RES 1 IN THE MIXED CULTURE

● ; VIABLE CELL COUNT OF <u>SHIGELLA FLEXNERI</u> IN THE SINGLE CULTURE

○ ; VIABLE CELL COUNT OF <u>SHIGELLA FLEXNERI</u> IN THE MIXED CULTURE

▲ ; VIABLE CELL COUNT OF <u>CLOSTRIDIUM BUTYRICUM</u> MII588-RES 1 IN THE MIXED CULTURE

● ;VIABLE CELL COUNT OF A DRUG-RESISTANT SHIGELLA STRAIN IN THE SINGLE CULTURE

○ ;VIABLE CELL COUNT OF A DRUG-RESISTANT SHIGELLA STRAIN IN THE MIXED CULTURE

▲ ;VIABLE CELL COUNT OF CLOSTRIDIUM BUTYRICUM MII588-RES 1 IN THE MIXED CULTURE

BIOLOGICAL INTESTINAL ANTISEPTICS

TECHNICAL FIELD

This invention relates to a novel biological intestinal antiseptic. More particularly, this invention relates to a biological intestinal antiseptic which contains, as the active component, cells or endospores of *Clostridium butyricum* MII588-Sens 1 strain having a sensitivity to a butyric-acid bacteriophage KMl, or cells or endospore of another *Clostridium butyricum* MII588-Res 1 strain which is a spontaneous mutant derived from the Sens 1 strain and which has gained resistance to the phage KM1. The antiseptic of this invention is useful for the prevention and therapeutic treatment of bacterial food-poisonings.

BACKGROUND ART

Among bacteriophages which infect *Clostridium bacteria* as obligatory anaerobes, the bacteriophage which was separated from *Clostridium tetani* by Cowels in 1934 was first known. Since then, bacteriophages capable of lysing various *Clostridium bacteria* have been reported. There are however rather few reports on such bacteriophages which lyse butyric-acid bacteria. It has been reported by Tahara et al. and Hongo et al. that one species of butyric-acid bacteria is lysed by the enzymes induced by phages HM3 and HM7 which infect *Clostridium saccharoperbutylacetonicum.* On the other hand, Schlechte described in 1980 such phage 5 which lyses oncolytic *Clostridium oncolyticum* M55 and *Clostridium butyricum* H8 {Schlechte, H. et al. "Archiv für Geschuwulstforschung", 50, 53–57 (1980)}.

The present inventors discovered the new bacteriophage KM1 which is totally different from these reported phages. Starting from this discovery, the present inventors further have found out a special butyric-acid bacterium, namely *Clostridium butyricum* MII588-Sens 1 strain having a sensitivity to the bacteriophage KM1 from amongst *Clostridium butyricum* MII588 strains, as well as a mutant, *Clostridium butyricum* MII588-Res 1 strain which is derived from the *Clostridium butyricum* MII588-Sens 1 strain and having gained a phage resistance. It has also been found by the present inventors that these strains, i.e., the Sens 1 and Res 1 strains exhibit, both in vitro and in vivo, a strong and stable antagonism against the causative bacteria of acute gastritis and enterocolitis, such as infectious bacteria of food-poisonings and enteric infections, enteropathogenic *Escherichia coli* and multiple-drug-resistant *Shigella strains.* Based on these findings, we have found that cells or endospores of the MII588-Sens 1 strain or the MII588-Res 1 strain are effective as an intestinal antiseptic or as a bacteriostatic agent against the causative bacteria of food-poisonings.

Bacteriophage KM1 was isolated from soil. Isolation, purification and biological characteristics of the bacteriophage KM1 have recently been reported in detail by Maeds, Ishii, Tanaka, Mikami and Arai {"J. General Microbiology", 132, 2271–2275 (1986)}.

The characteristics of this phage are as follows.

Shape and host range:

A regular plaque (lysed lesion) of bacteriophage KM1 is transparent and reaches 1–2 mm in diameter 24 hours after incubation. Under electron microscope using the negative staining method, bacteriophage KM1 is in the form of a tadpole and has a hexagonal head whose diameter is 60 nm. A tail having a contractile sheath has a length of 90 nm. Phage 5 of Schlechte et al., which was used for the sake of comparison, has an elliptical head whose diameter is 50×80 nm. Its tail is as long as 125 nm, has no sheath and is flexible. The G+C contents were 30.5 mol % for phage KM1 and 35.4 mol % for phage 5, which are both greater than the G+C contents (27–28 mol %) of standard *C. butyricum.* These two bacteriophages are clearly different from each other, because it is shown that when their DNAs are treated with restriction enzymes Bgl II, Eco RI and Hind III and the resultant DNA fragments are compared by an agarose gel electrophoresis, revealing that their electrophoresis patterns are entirely different. The DNA of phage 5 cannot be digested by Bgl II.

Bacteriophage KM1 cannot lyse entirely any of the butyric-acid bacteria which have been obtained from American Type Culture Collection (ATCC) of U.S.A., Institute of Fermentation, Osaka, and Institute of Applied Microbiology, University of Tokyo, etc. as well as *C. butyricum* H8 and oncolytic *C. oncolyticum* M55 (*C. butyricum* ATCC 13732) which have been supplied by Dr. Schlechte. On the other hand, phage 5 lysed *C. butyricum* IAM 19004, *C. butyricum* H8 and oncolytic *C. oncolyticum* M55.

*C. butyricum* MII588-Sens 1 and MII588-Res 1 strains are novel microorganisms isolated by the present inventors, and principal morphological and biochemical properties of these two strains may be summarized as shown in the following Tables 1 and 2, in comparison with those of a standard strain, namely, *C. butyricum* IAM 19001 strain which is stored in Institute of Applied Microbiology, University of Tokyo.

TABLE 1

Comparison in morphological properties between *Clostridium butyricum* MII5588-Sens 1 and Res 1 strains, and *Clostridium butyricum* IAM 19001

| | MII588-Sens 1 | MII588-Res 1 | IAM 19001 |
|---|---|---|---|
| Shape | Gram positive. Straight or slightly curved rod, and round at both ends. Size: 0.7–1.4 × 3.0–6.5 μm. Normally occurs as discrete cells. | Gram positive. Straight or slightly curved rod, and round at both ends. Size: 0.6–1.4 × 2.8–7.0 μm. Occurs as discrete cells, in pair and/or short chains. | Gram positive. Straight or slightly curved rod, and round at both ends. Size: 0.9–1.6 × 5.0–12.5 μm. Occurs as discrete cells, in pairs and/or short chains. |
| Motility | ++ | ++ | ++ |
| Flangella | Peritrichal | Peritrichal | Peritrichal |
| Endospores | Egg-shaped. 0.8–1.1 × 1.9–2.4 μm. Subterminal. | Egg-shaped. 1.0–1.1 × 1.9–2.3 μm. Subterminal. | Egg-shaped. 1.0–1.2 × 2.0–2.9 μm. Subterminal. |

TABLE 2

Comparison in biochemical properties between *Clostridium butyricum* MII588-Sens 1 and Res 1 strains, and *Clostridium butyricum* IAM 19001

| Biochemical Properties | MII588-Sens 1 | MII588-Res 1 | IAM 19001 |
|---|---|---|---|
| Sugar fermentations | | | |
| Sucrose | + | + | + |
| Raffinose | + | + | + |
| Lactose | + | + | + |
| Xylose | + | + | − |
| Glucose | + | + | + |
| Maltose | + | + | + |
| Rhamnose | − | − | − |
| Mannose | + | + | + |
| Arabinose | + | + | + |
| Ribose | + | + | − |
| Glycerol | + | + | − |
| Sorbitol | − | − | − |
| Dulcitol | − | − | − |
| Starch | + | + | + |
| Salicin | + | + | + |
| Diaminopimelic acid of Cell wall | DL | DL | DL |
| Litmus milk | Acidic, gas and coagulated | Acidic, gas and coagulated | Acidic, gas and coagulated |
| Sensitivity to bacteriophage KM1 | ++ | − | − |
| Reduction of nitrates | − | − | + |
| Optimum growth temperature | 37° C. | 37° C. | 37° C. |

*Clostridium butyricum* MII588-Sens 1 and Res 1 strains are spore-forming Gram-positive rods and are obligatory anaerobes. According to the Bergy's classification book "Bergy's Manual of Determinative Bacteriology", 8th edition, Williams & Wilkins Co., (1974), therefore, these two strains are thus classified to be comprised by either the genus Clostridium or the genus Desulfotomaculum. Since the present strains, namely, the Sens 1 and Res 1 strains do not reduce a sulfate in a lactate-sulfate medium, it is without question that they belong to the genus Clostridium. Moreover, their various morphological and biochemical properties are in substantial conformity with those of the butyric-acid bacterium *Clostridium butyricum* standard strain IAM 19001, as shown in the above Tables. IAM 19001 strain is, however, different from the description of "Bergy's Manual of Determinative Bacteriology" in that IAM 19001 strain lacks the ability for fermentation of xylose and ribose, and is also different from the MII588-Sens 1 and Res 1 strains in this respect. Although the IAM 19001 strain is also different from the MII588-Sens 1 and Res 1 strains with respect to their ability for the fermentations of glycerol, this is immaterial because some of the sugar fermentations is described to vary depending on each specific strain. The MII588-Sens 1 strain can be distinguished from the already known butyric-acid bacterium strains in that it is sensitive to bacteriophage KM1 and can be lysed by the latter phage.

DISCLOSURE OF THE INVENTION

In one aspect of this invention, there is provided a biological intestinal antiseptic which comprises, as the active component, cells or endospores of a butyricacid bacterium, *Clostridium butyricum* MII588-Sens 1 strain having such sensitivity that this strain is infected and lysed by bacteriophage KM1, or cells or endospores of a spontaneous mutant MII588-Res 1 strain which has been screened from the cultured colonies of the MII-588-Sens 1 strain and exhibits resistance to bacteriophage KM1.

*Clostridium butyricum* MII588-Sens 1 strain useful in th practice of this invention has been selected as a strain having the sensitivity to bacteriophage KM1, by cloning the parent strain, *Clostridium butyricum* MII588 strain (FERM BP-7765) (see the specification of Japanese Patent Application No. 174066/84 or Japanese Patent Application first publication "Kokai" No. 53219/86). The MII588-Res 1 strain has been obtained by mixing a large number of cells of the MII588-Sens 1 strain with bacteriophage KM1, coating the resultant mixture to an agar plate, incubating the cells there and then screening from the colonies subsequently grown.

The *Clostridium butyricum* MII5887-Sens 1 strain has been deposited with "Fermentation Research Institute" under FRI Deposit Number FERM P-9070 and also under FERM BP-1612 in terms of the Budapest Treaty, while *Clostridium butyricum* MII588-Res 1 strain has been deposited there under FRI Deposit Number FERM P-9069 and also under FERM BP-1611 in terms of the Budapest Treaty.

BEST MODE FOR WORKING THE INVENTION

Figure 1:
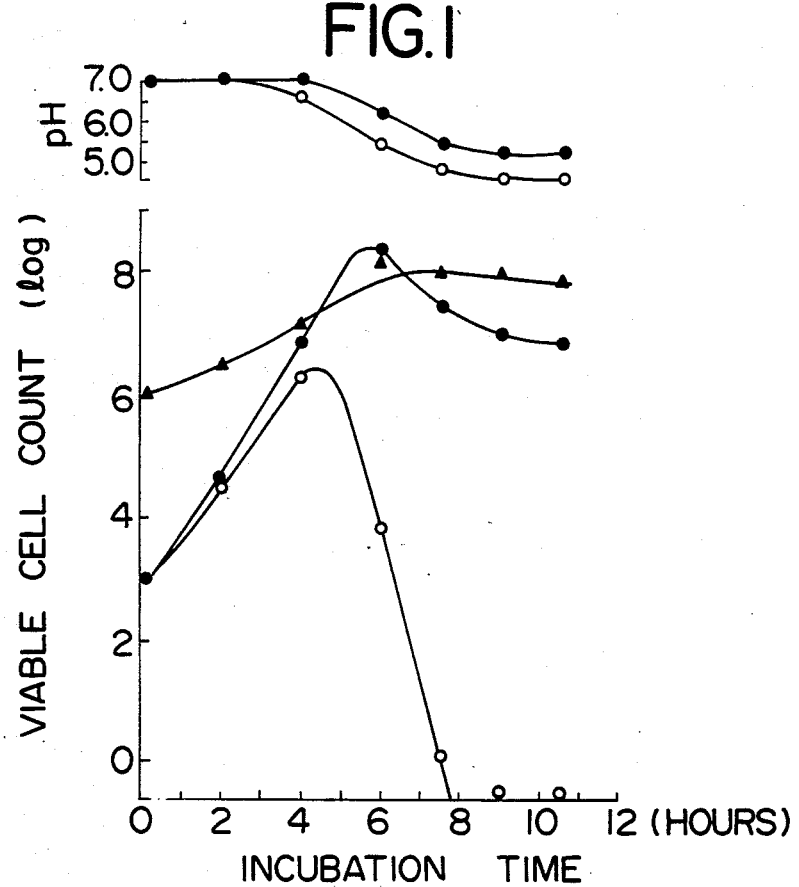
FIG. 1 is a diagrammatic representation which shows time-dependent variations in the viable cell counts (log) of *Vibrio parahaemolyticus* in its single culture and in its mixed culture in mixture with *Clostridium butyricum* MII588-Res 1 strain, and which also slows pH variations of the culture media.

When carrying out the production of an antiseptic according to this invention, *Clostridium butyricum* MII588Sens 1 or Res 1 strain which serves as the active component of the antiseptic can be cultured by any method which is employed routinely for the cultivation of obligatory anaerobes. A culture medium where extremely little formation of spores is permitted, for example, PYG medium is generally recommendable to provide the vegetative cells of the *Clostridium butyricum* strain. The composition of PYG medium may be described as illustrated below.

| Glucose | 20 g |
|---|---|
| Peptone | 20 g |
| Yeast extract | 10 g |
| Distilled water | 1000 ml |
| pH | 7.0 |

When cultured at 37° C. for 24 hours in this medium, most cells of the incubated strain are obtained in the form of vegetative cells.

On the other hand, CS medium may be used to provide the endospores. The composition of CS medium may be described as shown below.

| Corn starch | 20 g |
|---|---|
| Aqueous amino acid mixture | 20 g |
| CaCO$_3$ | 7.5 g |
| Distilled water | 1000 ml |
| pH | 7.0 |

The aqueous amino acid mixture is a slurry of strained soy sauce less residue ("AJIEKI", a product of Ajinomoto Co., Inc.). When the *C. butyricum* strain is cultured at 37° C. for 72 hours in this CS medium, at least 80% of the cells turn to the endospores.

When effecting the production of an antiseptic according to this invention, the above-described *C. butyricum* strain is cultured at a prescribed temperature for a predetermined period of time in the above-mentioned culture medium and the resulting culture broth is thereafter subjected to a centrifugal separator so as to harvest the cells. The thus-harvested cells are suspended in distilled water. After stirring the resultant suspension, it is subjected to a centrifugal separater to wash the cells. This procedure is repeated twice or thee times, and the cells ar then lyophilized into powder.

The cells or endospores in the powder form may usually be used as an antiseptic of this invention as they are, but they may further be mixed with a pharmaceutically acceptable ordinary excipient such as lactose or starch. They may also be admixed with a stabilizer and another medicament as needed, thereby formulating it into a dosage form. So long as the antiseptic of this invention is kept in such a state isolated from the surrounding air, by enclosing the antiseptic in ampoules, capsules or the like, no special conditions are required to store the antiseptic of this invention after its formulation into a dosage form. In use of the antiseptic of this invention, the cells or endospores may be administered orally at a dose of 0.5–2.5 g per day for adult.

A description will next be made of the activities of *C. butyricum* MII588-Sens 1 and MII588-Res 1 strains, which are employed in this invention, against food-poisoning bacteria and Shiqella strains.

Bacterial food-poisonings may be classified into infectious food-poisonings and toxin-induced food-poisonings. In the infectious food-poisonings, the causative bacteria present in the food orally enter the digestive tract with the food, and they grows there, whereby the symptoms of acute gastritis and/or enterocolitis occur. Effectiveness of the *C. butyricum* strain can be tested by tracing in vitro the antagonism of the *C. butyricum* strain against the causative bacteria. In contrast, in the case of such causative bacteria of the toxin-induced food-poisonings, the causative bacteria have already grown in the food and elaborated such toxins which can cause acute gastritis and/or enterocolitis. By the ingestion of the toxins present in the food, a man develops the disease. Accordingly, the medical efficacy on such toxin-induced food-poisonings must be determined by an absolutely different testing method.

Herein, descriptions are made with particular reference to *Vibrio parahaemolyticus*, *Salmonella enteritidis* and *Bacillus cereus* etc., as exemplary causative bacteria of the infectious food-poisonings.

1. Test of the antagonism of *C. butyricum* MII588-Sens 1 and Res 1 strains against the causative bacteria of food-poisonings:

Erlenmeyer flasks (100 ml capacity) were each filled with 100 ml of a glucose-added nutrient broth {comprising 0.5% glucose, 1.0% peptone, 0.5% NaCl (but 1.5% NaCl for *V. parahaemolyticus*), 0.5% meat extract}, followed by inoculation of the *C. butyricum* MII588-Sens 1 strain or Res 1 strain in an amount of $10^6$ cells/ml and a tested causative bacterium of the food-poisonings in an amount of $10^3$ cells/ml. They were stationarily cultured at 37° C. Time-dependent variations in viable cell count of each causative bacterium of the food-poisonings during the above culturing process were traced by counting the colonies of said bacterium on nutrient agar medium. Since it was extremely difficult to perform accurately the counting of the colonies in the case of counting the cells of *C. butyricum*, time-dependent variations in the viable cell count thereof were traced by means of a blood cell counting chamber.

In accordance with the above-described stationary culturing process, *Vibrio parahaemolyticus* was cultured singly and also in combination or mixture with *C. butyricum* MII588-Res 1 strain. Viable cells of the microorganisms on the respective incubated media were counted separately with the lapse of incubation time. Logarithmic values of the counts of viable cells (in term of CFU: colony-forming units) are plotted along the axis of ordinates, and the culture time is plotted along the axis of abscissas, whereby test results are exhibited by the diagrammatic curves shown in FIG. 1 of the accompanying drawings. Namely, FIG. 1 shows the time-dependent changes in pH value of the culture media and in the viable cell counts upon the single culture of *Vibrio parahaemolyticus* and upon the mixed culture of *C. butyricum* MII588-Res 1 strain and *Vibrio parahaemolyticus* in mixture. In FIG. 1, the curve connecting the closed circles indicates the viable cell counts obtained in the single culture of *Vibrio parahaemolyticus* as a tested bacterium, the curve connecting the open circles indicates the viable cell count of *Vibrio parahaemolyticus* obtained in its mixed culture, and the curve connecting the closed triangles indicates the viable cell counts of the MII588-Res 1 strain obtained in its mixed culture. Further, variations in pH values of the medium with the incubation time are also shown in the top of FIG. 1. The viable cell counts of the *C. butyricum* increased by about 100 times at an elapsed time of 7 hours after the beginning of the culture. In the case of culturing *Vibrio parahaemolyticus* singly, its rapid growth continued to reach a peak around 6 hours after the inoculation. When cultured in mixture with *C. butyricum* MII588-Res 1 strain, the viable cell counts of *Vibrio parahaemolyticus* reached the maximum in about 4 hours and *Vibrio parahaemolyticus* was then killed rapidly. Then, the pH value dropped to 4.6. This causative bacterium of the food-poisonings was also be killed in the same way as above when the MII588-Sens 1 strain and *Vibrio parahaemolyticus* were cultured in mixture. Substantially same results are also observed in the case of culturing *Bacillus cereus* singly, or in mixture.

Figure 2:
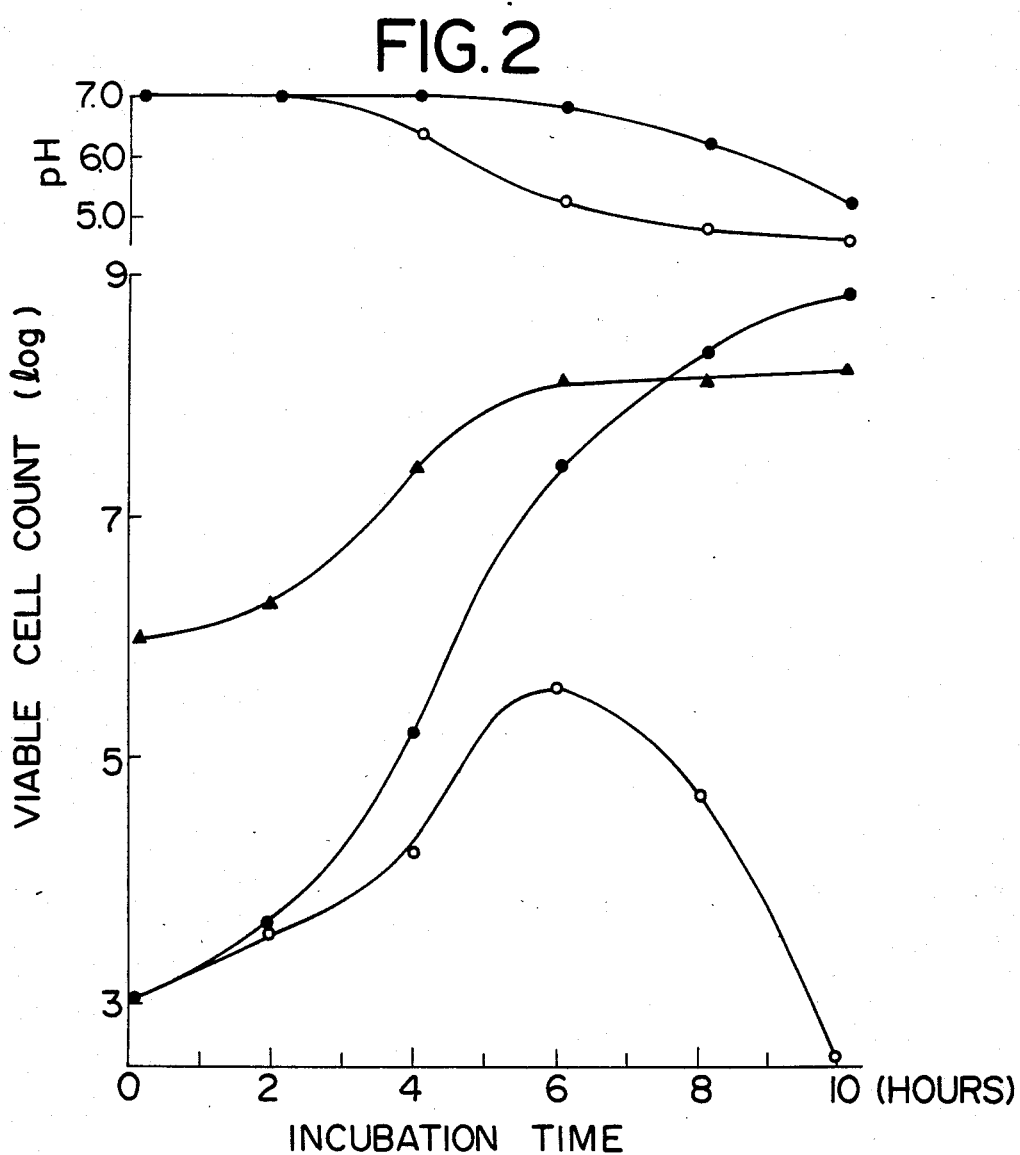
FIG. 2 is a diagrammatic representation which shows time-dependent variations in the viable cell counts (log) of *Salmonella enteritidis* in its single culture and in its mixed culture in mixture with *Clostridium butyricum* MII588-Res 1 strain, and which also shows pH variations of the culture media.
Figure 3:
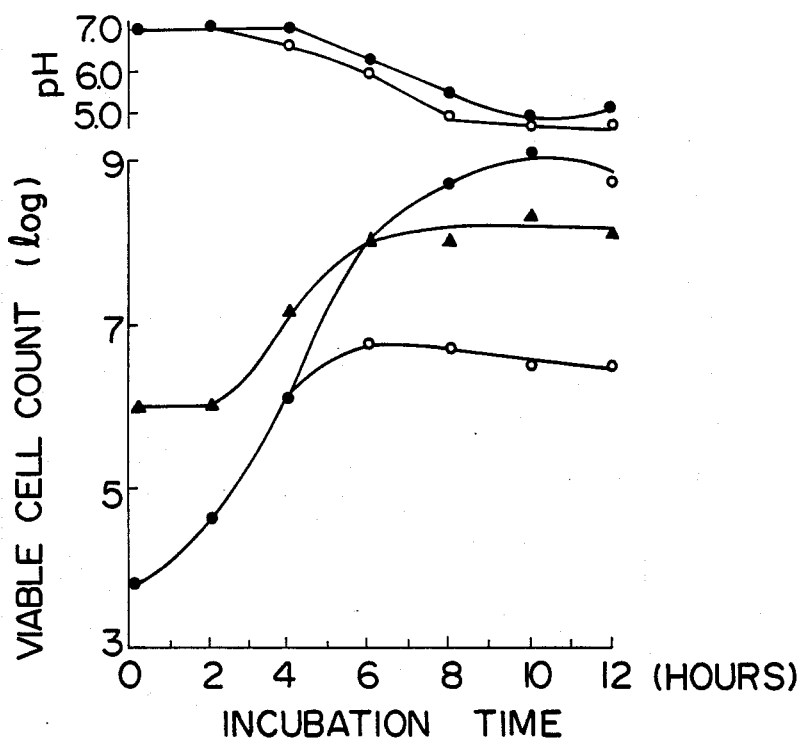
FIG. 3 is a diagrammatic representation which shows time-dependent variations in the viable cell counts (log) of enteropathogenic *Escherichia coli* in its single culture and in its mixed culture in mixture with *Clostridium butyricum* MII588-Res 1 strain, and which also shows pH variations of the culture media.
Figure 4:
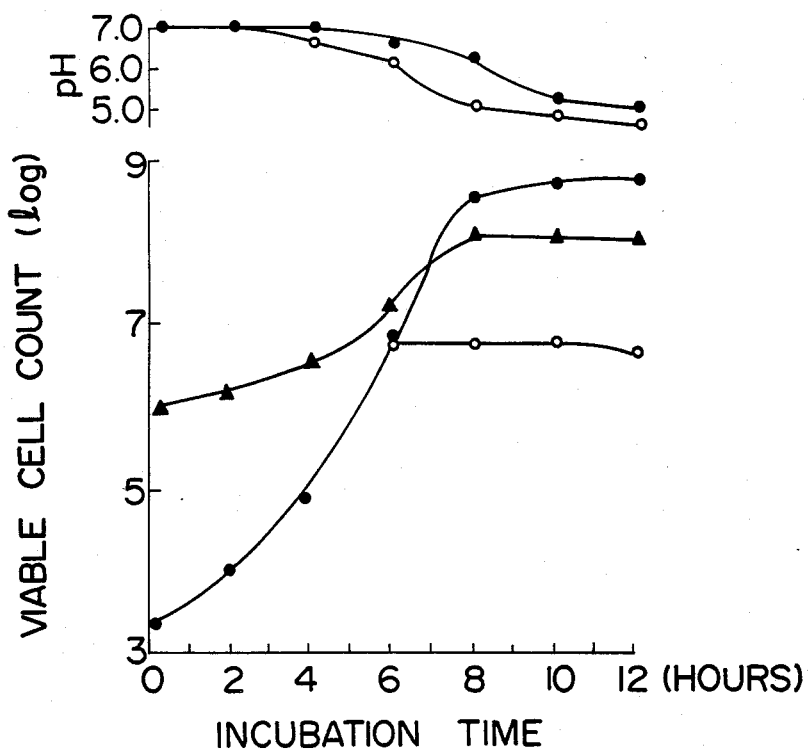
FIG. 4 is a diagrammatic representation which is similar to FIG. 3, but which relates to single culture of a *Shigella flexneri* strain and also to its mixed culture in mixture with *Clostridium butyricum* MII588-Res 1 strain.
Figure 5:
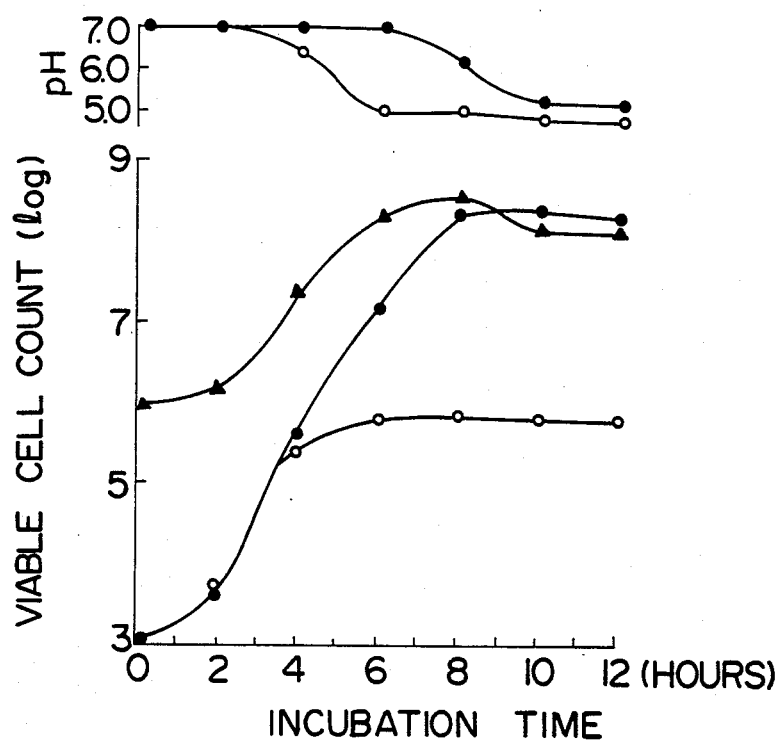
FIG. 5 is a diagrammatic representation which is similar to FIG. 3, but which relates to single culture of a multiple-drug-resistant *Shigel strain and also to it mixed culture in mixture with *Clostridium butyricum* MII588-Res 1 strain.
Figure 6:
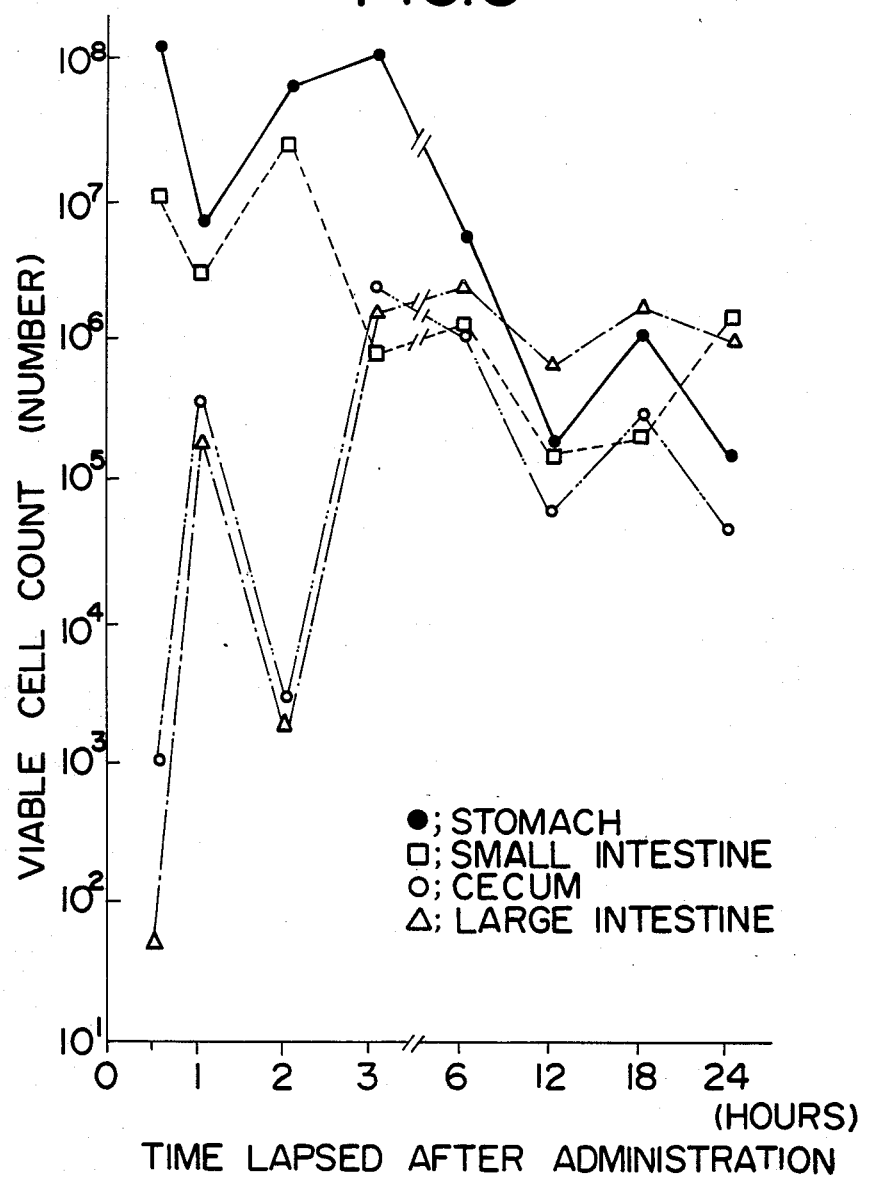
FIG. 6 is a diagrammatic representation of the distribution of viable cells, which illustrates time-dependent variations in the viable cell count of *Clostridium butyricum* MII588-Res 1 strain in different parts of the digestive tract of a hamster which was administered orally with endospores of the same *Clostridium butyricum* strain.

A similar test was also conducted using *Salmonella enteritidis* as a tested bacterium. Results of the test are also shown diagrammatically in FIG. 2. Namely, FIG. 2 illustrates time-dependent variations in the pH value and in the viable cell counts obtained in the single culture of *Salmonella enteritidis* and also in the mixed culture of *C. butyricum* MII588-Sens 1 strain and *Salmonella enteritidis* in mixture. When cultured in association with *C. butyricum* MII588-Sens 1 strain, the causative bacterium of the food-poisonings reached the maximum growth at a time of 6 hours after the inoculation and was killed thereafter. The killing of *S. enteritidis* was not so rapid as the above-described *Vibrio parahaemolyticus* or *Bacillus cereus.*

With respect to single culture of enteropathogenic *E. coli* and its mixed culture in mixture with *C. butyricum* MII588-Res 1 strain, the experiments were carried out in the same manner as above. The test results are also shown diagrammatically in FIG. 3. Namely, FIG. 3 illustrates time-dependent variations in the pH value and in the viable cell counts obtained in the single culture of the *E. coli* and also in the mixed culture of C. butyricum MII588-Res 1 strain and *E. coil* in mixture. In this case, the effect of the mixed culture was bacteriostatic, and the growth of the causative bacterium of the food-poisonings was suppressed strongly but the antibacterial activity against *E. coli* was not so remarkable as the aforementioned three species of the causative bacteria of the food-poisonings. Substantially same results were also obtained 15 with a single culture of a parent strain of *Shigella flexneri* and with the mixed culture of the *S. flexneri* parent strain in mixture with *C. butyricum* MII588-Res 1 strain (the test results obtained therefor are shown in FIG. 4), as well as with a single culture of a multiple-drug-resistant strain of *Shigella flexneri* and its mixed culture with *C. butyricum* MII588-Res 1 strain (the test results obtained therefor , are shown in FIG. 5). Namely, FIG. 4 shown time-dependent variations in the pH value and in the viable cell counts obtained in the single culture of the *Shigella flexneri,* as well as in the mixed culture of *C. butyricum* MII588-Res 1 strain with the *Shigella flexneri.* On the other hand, FIG. 5 depicts time-dependent variations in the pH value ad in the viable cell counts obtained in the single culture of the multiple-drug-resistant strain of *Shigella flexneri* as well as in the mixed culture of *C. butyricum* MII588-Res 1 strain with the multiple-drug-resistant strain of *Shigella flexneri.*

2. Test of intestinal localization of *C. butyricum* MII588-Sens 1 strain:

In order to allow the *C. butyricum* strain to exhibit the antagonism against such causative bacteria of the food-poisonings even in vivo in a living body, the *C. butyricum* must settle and live for a certain period of time in the digestive tract. The discovery of the novel bacteriophage KM1 and the *C. butyricum* MII588-Sens 1 strain has provided an extremely important means for the analyses of "in vivo" behaviors of the *C. butyricum* strain. Namely, the MII588-Sens 1 strain can be readily and accurately distinguished, identified and counted by testing its sensitivity to bacteriophage KM1 even when the MII588-Sens 1 strain is present along with many colonies of many other bacteria, including other strains of *C. butyricum,* within the contents of the digestive tract.

As a result of extensive investigations, the colistin-CS medium of the under-mentioned composition has been found to give very good results when it is used as a culture medium for incubating and screening the *C. butyricum* strain from the contents of digestive tract and culturing the same strain.

The colistin-CS medium is the medium of such composition as prepared by adding 800 μg/ml of colistin sodium methanesulfonate and 1.5% of agar to the CS medium given hereinbefore. A quantity of the digestive tract contents or feces is mixed with and incubated in the colistin-CS medium. This incubation may be conducted at 37° C. in a glove box under such an environment atmosphere comprising 80% $N_2$, 10% $CO_2$ and 10% $H_2$. Colonies which appear on the screening culture medium in 48-hours of incubation are mostly of *C. butyricum.* The colonies of the *C. butyricum* can be easily distinguished from the colonies of the other bacteria, because the former colonies can form the surrounding transparent zone wherein insoluble calcium carbonate precipitates have been dissolved by the produced organic acids mainly comprising butyric acid. Furthermore, when the colonies of *C. butyricum* are tested for their sensitivity to bacteriophage KM1, it is possible to distinguish and identify whether or not the tested colonies comprise the MII588-Sens 1 strain. By mean of the above procedures, the counting was periobically made of viable cells of the MII588-Sens 1 strain present in the contents of the stomachs, small intestines, cecums and large intestines of male golden hamsters of about 100 g body weight which had received oral administration of $8\times10^8$ endospores of *C. butyricum* MII588-Sens 1 strain, whereby the cell distribution of *C. butyricum* MII588-Sens 1 strain present in each part of the digestive tract was traced. Results of this test are diagrammatically depicted in FIG. 6. Thus, time-dependent variations in the viable cell counts of *C. butyricum* MII588-Sens 1 strain present in the digestive tract parts of the hamsters are represented in FIG. 6.

Until two hours after the administration of *C. butyricum* MII588-Sens 1 strain, this strain remained mostly within the stomach contents. Thereafter, the *C. butyricum* MII588-Sens 1 strain moved gradually therefrom to the small intestine and further to the cecum and large intestine. Six hours later, this *C. butyricum* strain was distributed almost evenly throughout the entire digestive tract with its population level of $10^5$–$10^6$ cells/g. This population level was kept constant approximately for 20 hours. In addition, *C. butyricum* MII588-Sens 1 strain present in feces was also assayed. Twenty four hours after a similar oral administration of the MII588-Sens 1 strain, $5\times10^7$ cells of *C. butyricum* MII588-Sens 1 strain were found per gram of feces.

3. Toxicity test:

An acute toxicity test for mice was conducted in the following manner.

Endospores of *C. butyricum* MII588-Sens 1 and Res 1 strains were separately administered to male DDY mice of 4-weeks age. Each group consisted of 10 mice and was tested by administration of the endospores at doses not greater than 500 mg/kg. None of the tested animals was killed at an of the doses of administration. During the observation for the period of 1 week, no visual abnormality was observed with the tested mice, and the body weight increases involved were not different from those for a control group of mice.

As has been demonstrated above, the *C. butyricum* strains used as the active components for biological intestinal antiseptics according to this invention can always exhibit stable and strong antiseptic and bacteriostatic activities against the food-poisoning bacteria. Moreover, the use of *C. butyricum* MII588-Res 1 strain can surprisingly avoid such accident that all the cells of the cultured MII588-Res 1 strain could suddenly be lysed and killed due to the contamination of bacteriophages from soil.

In another aspect of this invention, there is hence provided a method for treating *Vibrio parahaemolyticus*, *Salmonella enteritidis*, enteropathogenic *Escherichia coli* or *Shigella flexneri*, which comprises orally administering the cells or endospores of Clostridium butyricum MII588-Sens 1 strain or *Clostridiunm butyricum* MII588-Res 1 strain or both of them to an animal including a man, and thereby inhibiting the growth of *Vibrio parahaemolyticus*, *Salmonella enteritidis*, enteropathogenic *Escherichia coli* or *Shigella flexneri* that has entered accidentally in the intestinal tract of the animal, and also prohibiting the production of toxins in the intestinal tract by the pathogenic bacterium.

The present invention will hereinafter be illustrated specifically by the following Examples.

EXAMPLE 1

*Clostridium butyricum* MII588-Sens 1 strain (FRI Deposit Number FERM P-9070) was inoculated to 5 l of the CS medium and cultured at 37° C. for 72 hours. The endospores were collected by a cooled continuous centrifugal separator and then washed with distilled water, to recover 13.2 g of the wet cells. The cells were dried at 80° C. with hot air to obtain 2.7 g of the endospores as a powder. The dry endospores thus-obtained were sealed in 100 mg-portions into bials and then stored at 5° C. for 2 months. One of two groups of such male golden hamsters (10 hamsters per group) which had a body weight of about 100 g and had been inoculated orally with $10^5$ cells of *Salmonella enteritictis* was used as a control group, while the hamsters of the other group were orally administered with the dry endospores of the MII588-Sens 1 strain at a dose of $8 \times 10^8$ endospores at the end of 1 hour after the oral inoculation of the Salmonella species.

Three hours later, the animals were sacrificed and the abdominal cavity was opened, and *Salmonella enteritictis* present in the contents of the small intestine were incubated in the DHL-agar medium, followed by counting the number of the cells of the Salmonella species.

$10^3$ Cells/g of *Salmonella enteritictis* were found with the control group, whereas *Salmonella enteritictis* detected was in the level of 10 cells/g or less in the treated group of the hamsters which were administered with *C. butyricum* MII588-Sens 1 strain.

EXAMPLE 2

*C. butyricum* MII588-Res 1 strain (FRI Deposit Number FERM P-9069) was inoculated to 5 l of the CS medium and cultured at 37° C. for 72 hours. The endospores were collected by a cooled continuous centrifugal separator and then washed with distilled water, to recover 12.5 g of the wet cells. The cells were lyophilized to obtain 2.4 g of the endospores as a powder. The dry endospores thus-obtained were sealed in 100 mg-portions into bials and then stored at 5° C. for 2 months. Male golden hamsters (10 hamsters per group) having a body weight of about 100 g were orally inoculated with $10^5$ cells of *Vibrio parahemolyticus*. One group of hamsters was used as a control group, while the hamsters of the other group were orally administered with the dry endospores of the MII588-Res 1 strain at a dose of $8 \times 10^8$ endospores at the end of 1 hour after the inoculation of the Vibrio species.

Four hours later, the hamsters were sacrificed and subjected to the abdominal operation. *Vibrio parahaemolyticus* present in the contents of the large intestine of each hamster was incubated in BTB Teepole medium, and the cell number was counted. *Vibrio parahaemolyticus* was observed to grow to $3 \times 10^2$ cells/g with the control group, but *Vibrio parahaemolyticus* was not detected at all in the treated group which was administered with *C. butyricum* MII588-Res 1 strain.

INDUSTRIAL UTILITY OF THE INVENTION

As has been described above, the biological intestinal antiseptics of this invention are useful for the prevention and therapeutic treatment of bacterial food-poisonings in animals, including men.

Reference to Microorganisms Deposited under Rule 13.2

(a) Name and address of depository authority with which the microorganisms have been deposited:
Name: Fermentation Research Institute, Agency of Industrial Science and Technology, Ministry of International Trade and Industry
Address: 1-3, Higashi 1-chome, Tsukuba-shi, Ibaraki-ken, Japan (Mail Mo. 305).

(b) Date of the deposit with the depository authority (a): Dec. 5, 1986

(c) Accessible numbers allotted for the deposit by the depository authority (a):
BIKOKEN-JOKI No. 1611 (FERM BP-1611)
BIKOKEN-JOKI No. 1612 (FERM BP-1612)

We claim:

1. A biological intestinal antiseptic comprising, as the active component, cells or endospores of a butyric-acid bacterium *Clostridium butyricum* MII588-Sens 1 strain having the sensitivity that this strain is infected and lysed by bacteriophage KM1, or cells or endospores of a spontaneous mutant MII588-Res 1 strain which has been screened from the cultured colonies of the MII588-Sens 1 strain and exhibits resistance to bacteriophage KM1.

* * * * *